United States Patent
Kruse et al.

(10) Patent No.: US 6,218,582 B1
(45) Date of Patent: *Apr. 17, 2001

(54) METHOD FOR THE REDUCED FORMATION OF TERTIARY BUTYL ALCOHOL IN A FINISHING REACTOR IN THE MANUFACTURE OF METHYL TERTIARY BUTYL ETHER

(75) Inventors: Charles Joseph Kruse, Cypress; Kyle Lee Preston, Port Arthur; Brian Lawrence Benac, Austin, all of TX (US)

(73) Assignee: Huntsman International LLC, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/444,947

(22) Filed: May 19, 1995

(51) Int. Cl.[7] .................................................... C07C 41/09
(52) U.S. Cl. ........................... 568/697; 568/698; 568/699
(58) Field of Search ................................... 568/697, 698, 568/699

(56) References Cited

U.S. PATENT DOCUMENTS

| 4,144,138 | | 3/1979 | Rao et al. | 203/46 |
|---|---|---|---|---|
| 5,243,091 | * | 9/1993 | Kruse et al. | 568/697 |
| 5,292,964 | | 3/1994 | Gupta | 568/697 |
| 5,386,065 | * | 1/1995 | Kruse et al. | 568/698 |
| 5,387,721 | * | 2/1995 | Kruse et al. | 568/697 |
| 5,395,982 | * | 3/1995 | Cassata et al. | 568/699 |

* cited by examiner

*Primary Examiner*—Margaret G. Moore
(74) *Attorney, Agent, or Firm*—Russell R. Stolle; Ron D. Brown; Carl G. Ries

(57) ABSTRACT

A method for the preparation of methyl tertiary butyl ether is provided wherein a mixture of methanol and substantially peroxides-free tertiary butyl alcohol are catalytically reacted to form a reaction product comprising unreacted methanol, unreacted tertiary butyl alcohol, water, isobutylene and methyl tertiary butyl ether, that is separated into a substantially anhydrous first lighter distillation fraction comprising isobutylene, methanol and methyl tertiary butyl ether and a second heavier distillation fraction comprising methanol, tertiary butyl alcohol and water, and wherein the isobutylene and methanol in the first distillation fraction are reacted to form an isobutylene conversion product that contains additional methyl tertiary butyl ether that is substantially free from tertiary butyl alcohol.

7 Claims, 1 Drawing Sheet

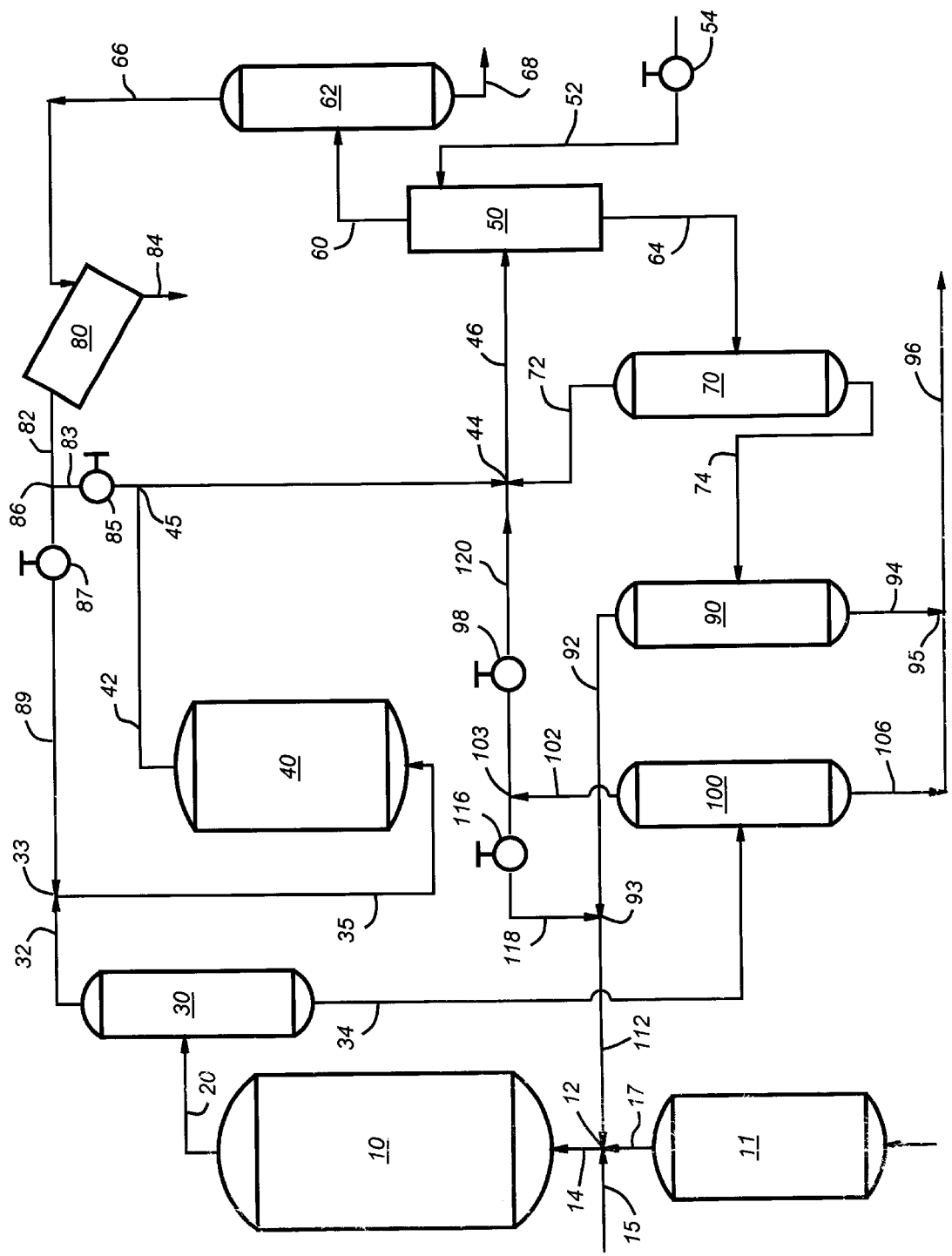

US 6,218,582 B1

METHOD FOR THE REDUCED FORMATION OF TERTIARY BUTYL ALCOHOL IN A FINISHING REACTOR IN THE MANUFACTURE OF METHYL TERTIARY BUTYL ETHER

BACKGROUND OF THE INVENTION

1. Technical Field of the Invention

This invention relates to a process for the manufacture and purification of methyl tertiary butyl ether. More particularly, this invention relates to a process for reducing the formation of tertiary butyl alcohol in a finishing reactor in a process for the manufacture of methyl tertiary butyl ether (MTBE) from tertiary butyl alcohol (TBA) and methanol (MeOH). Still more particularly, this invention relates to a process for the manufacture of MTBE from TBA and MeOH wherein by-product isobutylene formed by the reaction of TBA with MeOH is reacted with methanol in a finishing reactor under substantially anhydrous conditions to selectively provide additional methyl tertiary butyl ether with the reduced formation of tertiary butyl alcohol.

2. Prior Art

In U.S. Pat. No. 4,144,138 (1979) to Rao et al., there is disclosed a method for recovering methyl tertiary butyl ether from etherification reaction effluent by azeotropic distillation to recover methanol-ether azeotrope overhead which is water-washed to give pure ether extract, the latter being azeotropically distilled to yield ether-methanol overhead which is recycled to water washing.

The preparation of methyl tert-butyl ether from methyl and tert-butyl alcohols is discussed in S. V. Rozhkov et al., Prevrashch Uglevodorodov, Kislotno-Osnovn. Geterogennykh Katal. Tezisy Dokl., Vses. Konf., 1977, 150 (C. A. 92:58165y). Here the TBA and methanol undergo etherification over KU-2 strongly acidic sulfopolystyrene cation-exchangers under mild conditions. This reference contains data on basic parameters of such a process.

Kruse et al. U.S. Pat. No. 5,243,091 discloses a method for the preparation of methyl tertiary butyl alcohol wherein a mixture of methanol and tertiary butyl alcohol are catalytically reacted to form a reaction product that is separated into a first lighter distillation fraction comprising isobutylene, methanol and methyl tertiary butyl ether and a second heavier distillation fraction comprising methanol, tertiary butyl alcohol and water, wherein the first distillation fraction and a first recycle isobutylene fraction are reacted to form an isobutylene conversion product that is charged, together with recycle isobutylene to a methanol extraction zone and countercurrently contacted with water to provide an overhead raffinate comprising aqueous isobutylene, and wherein the isobutylene is recovered and recycled.

Gupta U.S. Pat. No. 5,292,964 discloses a method for the preparation of methyl tertiary butyl ether wherein a mixture of methanol and tertiary butyl alcohol are catalytically reacted to form a reaction product containing the water of etherification and at least one mol of methanol per two moles of methyl tertiary butyl ether, wherein the reaction product is fractionated to separate a lighter methanol and methyl tertiary butyl ether fraction from the water and tertiary butyl alcohol and wherein the methanol in the lighter distillation fraction is reacted with isobutylene to form additional methyl tertiary butyl ether.

Gupta states that it is essential to provide a reaction product containing at least one mol of methanol per two moles of methyl tertiary butyl ether, so that water is separable from the methyl tertiary butyl ether in the fractionating column to provide a lighter distillation fraction substantially free from water.

BACKGROUND INFORMATION

Methyl tert-butyl ether is finding increasing use as a blending component in high octane gasoline as the current gasoline additives based on lead and manganese are phased out.

It is known to react methanol with tertiary butyl alcohol in the presence of a catalyst in order to produce methyl tertiary butyl ether. A wide variety of catalysts have been suggested for this purpose.

In U.S. Pat. No. 2,282,469 to Frolich there is disclosed a process for preparing methyl tertiary butyl ether over a catalyst comprising Kieselguhr impregnated with phosphoric acid at a temperature of about 175° F. to 350° F.

Japanese Patent 0007432 teaches the use of zeolites to make dialkyl ethers containing primary or secondary alkyl groups. The zeolites have a porous structure and are represented by:

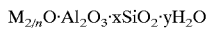

$$M_{2/n}O \cdot Al_2O_3 \cdot xSiO_2 \cdot yH_2O$$

where M is an alkali metal or alkaline earth metal cation or organic base cation, n is the valence of the cation and x and y are variables.

U.S. Pat. No. 4,058,576 to Chang et al. teaches the use of (pentasil-type) aluminosilicate zeolites, such as ZSM-5, having a pore size greater than 5 angstrom units and a silica-to-alumina ratio of at least 12, to convert lower alcohols to a mixture of ethers and olefins.

In U.S. Pat. No. 4,822,921 there is disclosed a method for producing MTBE by reacting tertiary butyl alcohol and methanol in the presence of a catalyst comprising an inert support, such as titania, having a phosphoric acid impregnated thereon.

U.S. Pat. No. 4,827,048 discloses a method for producing MTBE by reacting tertiary butyl alcohol and methanol in the presence of a catalyst comprising a heteropoly acid such as 12-tungstophosphoric acid or 12-molybdophosphoric acid on an inert support, such as titania.

Two of the principal by-products formed during the reaction of the methanol with the tertiary butyl alcohol are water and isobutylene. Methanol and methyl tertiary butyl ether form an azeotrope which is broken only with difficulty and therefore the separation of methanol from MTBE during the recovery of purified methyl tertiary butyl ether presents a serious problem.

In U.S. Pat. No. 4,820,877, separation of methanol from MTBE is accomplished by using a refinery fuel gas to enhance the separation of methanol into the overhead stream of a distillation column.

In U.S. Pat. No. 4,814,517, separation of methanol from MTBE is accomplished by using a silica gel to preferentially adsorb methanol from an MTBE stream and by periodically regenerating the silica gel.

In U.S. Pat. No. 4,798,674, separation of methanol from MTBE is accomplished by using a membrane of cross-linked polyvinyl alcohol or a quaternary ammonium ion resin. Methanol preferentially permeates through the membrane increasing the MTBE concentration of the charge liquid.

In U.S. Pat. No. 4,759,850, separation of methanol from MTBE is accomplished by reverse osmosis.

In U.S. Pat. No. 4,440,963, separation of methanol from MTBE is accomplished by adding an agent such as 2-methyl pentane or Freon 113 to form an azeotrope with methanol. This azeotrope is recovered overhead giving a methanol-free MTBE bottoms product.

As recognized by Rao et al. in U.S. Pat. No. 4,144,138, isobutylene is formed as a by-product when methanol is reacted with tertiary butyl alcohol. In accordance with the Rao process, the isobutylene is separated from the reaction product in an initial azeotropic distillation step as a noncondensable gas. Rao teach that the part of the isobutylene may be flashed from the reaction product for recycle, depending upon purity.

SUMMARY OF THE INVENTION

This invention relates to a process for the manufacture of MTBE from TBA and MeOH wherein by-product isobutylene formed by the reaction of TBA with MeOH is reacted with methanol in a finishing reactor under substantially anhydrous conditions to selectively provide additional methyl tertiary butyl ether with the reduced formation of tertiary butyl alcohol.

A preferred process for reducing the formation of tertiary butyl alcohol in a finishing reactor in the manufacture of methyl tertiary butyl ether (MTBE) from tertiary butyl alcohol (TBA) and methanol (MeOH) comprises the steps of:

a) continuously passing a feed mixture comprising substantially peroxides-free tertiary butyl alcohol and methanol through a methyl tertiary butyl ether etherification reaction zone containing a bed of a TBA/MeOH etherification catalyst under etherification reaction conditions to form an etherification reaction product comprising unreacted methanol, unreacted tertiary butyl alcohol, water, isobutylene (IBTE) and methyl tertiary butyl ether, b) continuously charging the etherification reaction product to a methyl tertiary butyl ether distillation zone and separating it therein into a substantially anhydrous first lighter distillation, substantially TBA free fraction comprising isobutylene, methanol and methyl tertiary butyl ether (i.e., 0.05 to 0.2 wt. % water) and a second heavier distillation fraction comprising methanol, tertiary butyl alcohol and water, c) continuously charging the first distillation fraction to a finishing reactor containing a solid resin IBTE/MeOH etherification catalyst and reacting the isobutylene and methanol to form an isobutylene conversion product comprising methyl tertiary butyl ether, unreacted methanol, unreacted isobutylene and less than 1 wt. % of tertiary butyl alcohol.

When tertiary butyl alcohol is prepared from tertiary butyl hydroperoxide the tertiary butyl alcohol reaction product will contain minor amounts of peroxide contaminants such as tertiary butyl hydroperoxide, ditertiary butyl peroxide, allyl tertiary butyl peroxide, etc. When tertiary butyl alcohol contaminated with minor amounts of peroxides is reacted with methanol to form methyl tertiary butyl ether, the etherification reaction product resulting from the reaction will contain the peroxide contaminants.

In accordance with an embodiment of the present invention, a peroxides-contaminated tertiary butyl alcohol feed-stock is passed through a peroxides decomposition reaction zone before being charged to the methyl tertiary butyl ether etherification reaction zone so that the methyl tertiary butyl ether etherification product will be substantially free from peroxide contaminants.

In accordance with a further embodiment of the present invention, an integrated process is provided wherein a peroxides-contaminated tertiary butyl alcohol feedstock is passed through a peroxides decomposition reaction zone to substantially completely decompose the peroxide contaminants contained therein, and then charged to a methyl tertiary butyl ether etherification reaction zone together with methanol to form an isobutylene-containing methyl tertiary butyl ether etherification product that is substantially free from peroxide contaminants, wherein by-product isobutylene is utilized downstream of the etherification reaction zone as an extractant in the purification of the methyl tertiary butyl ether and wherein the by-product isobutylene is used as a reactant in the preparation of additional methyl tertiary butyl ether.

DESCRIPTION OF PREFERRED EMBODIMENTS

I

In accordance with a preferred embodiment of the present invention, a method for the continuous preparation of methyl tertiary butyl ether (MTBE) from tertiary butyl alcohol (TBA) and methanol (MeOH) is provided comprising the steps of:

a) continuously charging a peroxides-contaminated tertiary butyl alcohol feedstock to a peroxides decomposition reaction zone and substantially completely decomposing the peroxide contaminants therein to form a substantially peroxides-free tertiary butyl alcohol product, b) continuously charging a reaction feed mixture comprising methanol and the substantially peroxides-free tertiary butyl alcohol product to an etherification reaction zone containing a bed of a TBA/MeOH etherification catalyst and reacting said reaction feed mixture therein to form an etherification reaction product comprising unreacted methanol, unreacted tertiary butyl alcohol, water, isobutylene and methyl tertiary butyl ether, c) continuously charging the etherification reaction product to a first methyl tertiary butyl ether distillation zone and separating it therein into a first lighter substantially anhydrous distillation fraction comprising isobutylene, methanol and methyl tertiary butyl ether and a second heavier distillation fraction comprising methanol, tertiary butyl alcohol and water, d) continuously charging an isobutylene reaction mixture comprising the first distillation fraction and a first recycle isobutylene (IBTE) fraction to an isobutylene conversion reaction zone containing a solid resin IBTE/MeOH etherification catalyst and reacting the isobutylene with methanol therein to form an isobutylene conversion product, e) continuously charging an extraction feed mixture comprising the isobutylene conversion product and a second isobutylene recycle fraction to a methanol extraction zone and countercurrently contacting the extraction feed mixture therein with water to provide an overhead raffinate comprising isobutylene, methyl tertiary butyl ether and a minor amount of water, and a extract comprising methanol, water and a minor amount of methyl tertiary butyl ether, f) continuously charging the raffinate to a second methyl tertiary butyl ether distillation zone and separating it therein into a third lighter distillation fraction comprising isobutylene and water and a fourth heavier distillation fraction consisting essentially of methyl tertiary butyl ether, g) continuously charging the third distillation fraction to a decantation separation zone and separating it therein into a substantially anhydrous isobutylene fraction and a water fraction, h) continuously recycling a first portion of said isobutylene fraction to the isobutylene reaction conversion zone as the first isobutylene recycle fraction, and i) continuously recycling a second portion of said isobutylene fraction to the methanol extraction zone as the second isobutylene recycle fraction.

DETAILED DESCRIPTION OF THE PRESENT INVENTION

The Etherification Reaction Catalyst

In accordance with the MTBE manufacture and purification method of the present invention, an etherification reaction zone containing a bed of etherification catalyst is utilized. A wide variety of etherification catalysts can be used for this purpose, such as supported phosphorus acid-type catalysts. A preferred catalyst is a sulfonic acid resin etherification catalyst such as a sulfonated polystyrene resin cross-linked with divinyl benzene.

Any suitable solid resin etherification catalyst may be used for this purpose, such as a strongly acidic ion exchange resin consisting essentially of sulfonated polystyrene, such as a divinyl benzene crosslink polystyrene matrix containing from about 0.5 to about 20% of copolymerized divinyl benzene. Resins of this nature are manufactured and sold commercially under various trade names such as "Dowex 50", "Nalcite HCR" and "Amberlyst 15". The use of catalyst of this nature is disclosed, for example, in Rao U.S. Pat. No. 4,144,138.

Also, Kieselguhr impregnated with phosphoric acid as disclosed in Frolich U.S. Pat. No. 2,282,469, titania having phosphoric acid impregnated thereon as disclosed in Knifton U.S. Pat. No. 4,822,921, a hetero polyacid such as 12-tungstophosphoric acid or 12-molybdophosphoric acid supported on titania, etc., may be used.

Zeolites as disclosed in Japanese Patent 0007432 or aluminosilicate zeolites as disclosed in Chang et al. U.S. Pat. No. 4,058,576 may also be used.

The reaction conditions to be utilized when reacting methanol with tertiary butyl alcohol in the presence of a sulfonic acid resin etherification catalyst of the type disclosed in the prior art include a reaction temperature of about 70° to about 140°C., a pressure of about 30 to about 500 psia and a space velocity of about 0.5 to about 20 volumes of feed per volume of etherification catalyst per hour.

The Solid Resin Etherification Catalyst

In accordance with the present invention, a substantially anhydrous distillate fraction is obtained during the recovery process, identified above as the first distillation fraction, and which contains both isobutylene and methanol is brought into contact with a solid resin etherification catalyst, as described above, in order to convert a significant portion of the isobutylene and methanol to methyl tertiary butyl ether.

The first distillation fraction will normally contain from about 0.05 to about 0.2 wt. % of water from about 5 to about 10 wt. % of isobutylene, from about 70 to about 80 wt. % of methyl tertiary butyl ether and from about 10 to about 20 wt. % of methanol.

An isobutylene reaction mixture is prepared from the first distillation fraction and a first isobutylene recycle fraction so as to provide an isobutylene reaction mixture containing about an additional 1 to 10 wt. % of isobutylene, based on the weight of the first distillation fraction. Thus, the isobutylene reaction mixture may comprise from about 6 to about 15 wt. % of isobutylene, from about 65 to about 75 wt. % of methyl tertiary butyl ether and from about 10 to about 20 wt. % of methanol.

Any suitable solid resin etherification catalyst may be used for this purpose, such as a strongly acidic ion exchange resin consisting essentially of sulfonated polystyrene, such as a divinyl benzene crosslink polystyrene matrix containing from about 0.5 to about 20% of copolymerized divinyl benzene. Resins of this nature are manufactured and sold commercially under various trade names such as "Dowex 50", "Nalcite HCR" and "Amberlyst 15". The use of catalyst of this nature is disclosed, for example, in Rao U.S. Pat. No. 4,144,138.

The first distillation fraction will normally contain from about 0.05 to about 0.2 wt. % of water, from about 5 to about 10 wt. % of isobutylene, from about 70 to about 80 wt. % of methyl tertiary butyl ether and from about 10 to about 20 wt. % of methanol.

It is brought into contact with a solid resin etherification catalyst in the isobutylene conversion reaction zone under conversion conditions including, for example, a temperature of about 35° to about 130° C., a pressure of about 30 to about 500 psia and a contact time of about 0.5 to about 20 volumes of first distillate fraction per volume of etherification catalyst per hour. As a consequence, an isobutylene conversion product is formed which will normally contain from about 0 to about 10 wt. % of isobutylene, about 75 to about 85 wt. % of methyl tertiary butyl ether and from about 10 to about 15 wt. % of methanol and about 0 to about 2 wt. % of tertiary butyl alcohol.

Peroxide Decomposition

When the tertiary butyl alcohol feedstock to be used in the preparation of methyl tertiary butyl ether is tertiary butyl alcohol contaminated with peroxides such as tertiary butyl hydroperoxide, ditertiary butyl peroxide, allyl tertiary butyl peroxide, etc., the feedstock is treated for the substantially complete removal of the peroxide contaminants before it is charged to the methyl tertiary butyl ether etherification zone.

It is known to prepare tertiary butyl alcohol by the thermal or catalytic decomposition of tertiary butyl hydroperoxide. It is also known to prepare tertiary butyl alcohol by the catalytic reaction of tertiary butyl hydroperoxide with propylene to form propylene oxide and tertiary butyl alcohol. The tertiary butyl alcohol feedstock derived from tertiary butyl hydroperoxide in this manner will contain peroxide contaminants. A typical feedstock prepared in this fashion will contain from about 95 to 99 wt. % of tertiary butyl alcohol and less than about 2.0 wt. % of peroxide contaminants.

In accordance with the present invention, the peroxides-contaminated tertiary butyl alcohol is charged to a peroxides decomposition reaction zone where the peroxides are substantially completely thermally and/or catalytically decomposed. The peroxide contaminants will be decomposed to form water and tertiary butyl alcohol, and trace amounts of other decomposition products such as acetone and methyl formate.

When the peroxides are to be thermally decomposed, the peroxides-contaminated tertiary butyl alcohol feedstock is continuously passed through a reactor in the peroxides decomposition reaction zoned at a temperature of about 100° to about 200° C., a pressure of about 80 to about 500 psia at a flow rate of about 0.5 to 20 volumes of feedstock per reactor volume per hour to thereby provide a substantially peroxides-free tertiary butyl alcohol reaction product.

Alternately, the peroxide contaminants may be catalytically decomposed.

A wide variety of catalysts may be used for this purpose, such as cobalt borate as disclosed in U.S. Pat. No. 4,547,598, a nickel, copper, chromia catalyst as disclosed in Sanderson et al. U.S. Pat. No. 4,704,482, an iron, copper, chromia, cobalt catalyst as disclosed in Sanderson et al. U.S. Pat. No. 4,705,903, a base treated hydrogenation catalyst from groups VIB or VIIIB of the Periodic Table as disclosed in Sanderson et al. U.S. Pat. No. 4,742,179, a nickel, copper, chromium and barium catalyst as disclosed in Sanderson et al. U.S. Pat. No. 4,873,380, a metal phthalocyanine catalyst as disclosed in Sanderson et al. U.S. Pat. No. 4,910,349, an imidazole-promoted methyl metal phthalocyanine catalyst as disclosed in Sanderson et al. U.S. Pat. No. 4,912,266, a base promoted metal phthalocyanine catalyst as disclosed in Sanderson et al. U.S. Pat. No. 4,912,267, a solid ruthenium catalyst as disclosed in Sanderson et al. U.S. Pat. No. 4,922,033, a promoted metal porphine catalyst as disclosed in Sanderson et al. U.S. Pat. No. 4,922,034, etc.

The conversion conditions to be utilized in the peroxide decomposition zone may comprise, for example, a temperature of about 100° to about 200° C., a pressure of about 80 to about 500 psia and a space velocity of about 0.5 to about 20 volumes of feed per volume of catalyst per hour.

The effluent from the peroxide decomposition zone will typically comprise about 95 to about 99 wt. % of tertiary butyl alcohol and less than about 0.1 wt. % of peroxide contaminants.

BRIEF DESCRIPTION OF THE DRAWING

The drawing is a schematic flow sheet with conventional parts omitted showing the general reaction and recovery sequence of the present invention for the manufacture and purification of methyl tertiary butyl ether.

DESCRIPTION OF THE PREFERRED EMBODIMENT

Turning now to the drawing, there is shown a schematic flow sheet illustrating the preferred method for the practice of the process of the present invention. In the drawing, conventional parts, such as valves, pumps, temperature control sensors, pressure sensors, heaters, coolers, flow control regulation apparatus, reflux condenses, reboilers, etc., have been omitted.

In accordance with the present invention, there is provided an etherification reaction zone 10 containing a bed of solid etherification catalyst. Any suitable etherification catalyst may be used such as, for example, a solid resin etherification of the type described above, such as a strongly acidic ion exchange resin consisting essentially of sulfonated polystyrene crosslinked with divinyl benzene (e.g., Dowex 50, Nalcite HCR, Amberlyst 15, etc.). As another example, the catalyst may be a fluorophosphoric acid-on-titania catalyst of the type disclosed in Knifton et al. U.S. Pat. No. 4,822,921 or a heteropoly acid such as 12-tungstophosphoric acid or 12-molybdophosphoric acid supported on an inert support such as titania.

When the tertiary butyl alcohol is prepared by the thermal or catalytic decomposition of tertiary butyl hydroperoxide, it will contain minor amounts of impurities such that, for example, the feedstock charged to the reaction 10 will contain the following components:

ETHERIFICATION REACTION ZONE FEED MIXTURE

| Component | wt. % (approximate) |
|---|---|
| Methanol | 40.0 |
| TBA[1] | 48.0 |
| Acetone | 0.6 |
| 2-Propanol | 5.5 |
| MTBE[2] | 0.2 |
| DTBP[3] | 0.1 |
| t-Butyl Formate | 0.1 |
| Water | 5.5 |

[1]Tertiary butyl alcohol
[2]Methyl tertiary butyl ether
[3]Ditertiary butyl peroxide When the tertiary butyl alcohol feedstock to be initially charged to etherification reaction zone 10 is a peroxides-contaminated tertiary butyl alcohol feedstock, as described above, the tertiary butyl alcohol feedstock is initially charged by way of a tertiary butyl alcohol feed line 13 to a peroxides decomposition zone 11, such as, for example a thermal peroxides decomposition zone 11, operated (e.g.) at a temperature of about 100° to about 200° C., a pressure of about 80 to about 500 psia and a flow rate of about 0.5 to 20 volumes of feedstock per reactor volume per hour to thereby provide a substantially peroxides-free tertiary butyl alcohol reaction product. The peroxide contaminants will be decomposed to form water and tertiary butyl alcohol, and trace amounts of other decomposition products such as acetone and methyl formate.

The substantially peroxides-free tertiary butyl alcohol reaction product is continuously discharged from the peroxides decomposition zone 11 by a discharge line 17 leading to a manifold 12. Fresh methanol is continuously charged to the manifold 12 by a line 15, as is a recycle stream 112 containing recycle methanol and recycle tertiary butyl alcohol. The flow of methanol and tertiary butyl alcohol to the manifold 12 through the lines 15, 17 and 112 is regulated so that a molar excess of methanol is present in the line 14 leading to the etherification reaction zone 10, such as, for example, a molar ratio of about 1.1 to about 3 moles of methanol per mol of tertiary butyl alcohol.

Within the etherification reaction zone 10, the feed mixture is brought into contact with the bed of etherification catalyst, such as a sulfonic acid resin etherification catalyst under reaction conditions including a pressure of about 30 to about 500 psia, and more preferably from about 200 to about 300 psia, a temperature of about 30° to about 200° C., and more preferably from about 70° to about 140° C., and still more preferably from about 80° to about 120° C. When the catalyst is a supported phosphorus acid-type catalyst, the reaction temperature may suitably be in the range of about 150° to about 190° C.

Contact time within the etherification reaction zone is suitably such that about 0.5 to about 20 volumes of feed mixture per volume of etherification catalyst per hour are fed to the etherification reaction zone 10 and, more preferably from about 1 to about 4 volumes of feed mixture per volume of etherification catalyst per hour.

Within the etherification reaction zone 10, methanol will exothermically react with the tertiary butyl alcohol to form methyl tertiary butyl ether which will be contained in a reaction product discharged from the etherification reaction zone 10 by way of a line 20 leading to a first methyl tertiary butyl ether (MTBE) distillation zone 30.

As a specific example, when the solid etherification catalyst is a sulfonic acid resin such as Amberlyst 15 and when the molar ratio of methanol to tertiary butyl alcohol in the feed mixture charged to the etherification reaction zone 10 by the line 14 is within the ratio of about 2.0 moles of methanol per mole of tertiary butyl alcohol, and the reaction is conducted at a temperature of about 100° C. at a feed rate of about 2.0 volumes of feed mixture per volume of catalyst per hour, the etherification reaction product may have the composition in part shown by the following table:

| ETHERIFICATION REACTION PRODUCT | |
|---|---|
| Component | % |
| Water | 13.7 |
| Methanol | 27.6 |
| Isobutylene | 3.5 |
| TBA[1] | 14.1 |
| MTBE[2] | 34.5 |
| Other[3] | 6.6 |

[1]Tertiary butyl alcohol
[2]Methyl tertiary butyl ether
[3]Includes the acetone, propanol, ditertiary butyl peroxide, tertiary butyl formate, etc. initially present in the tertiary butyl alcohol feedstock.

The etherification reaction product charged to the first MTBE distillation zone 30 by way the charge line 20 is fractionated therein under distillation conditions including a liquid reflux temperature of about 40° to about 80° C., a reflux ratio of about 1.0 to about 1.5, a reboiler temperature of about 95° to about 105° C., and a pressure of about 15 to about 60 psia, the distillation condition being selected such that substantially all of the MTBE in the etherification reaction product 20 is taken overhead from the first distillation zone 30 by a line 32 and such that substantially all of the water exits the distillation zone by the line 34. As a consequence, the first distillation fraction 32 taken overhead from the distillation zone 30 will be substantially anhydrous and will comprise substantially all of the isobutylene and substantially all of the methyl tertiary butyl ether and some of the methanol charged to the first distillation zone 30. The second heavier distillation fraction 34 discharged from the first MTBE distillation zone 34 will comprise methanol, tertiary butyl alcohol and water.

In accordance with the present invention, the first distillation fraction 32 in admixture with recycle isobutylene added by a recycle line 89 is charged by way of manifold 33 and charge line 35 to an isobutylene conversion zone 40 containing a bed of solid resin etherification catalyst such as a bed of Amberlyst 15 sulfonated polystyrene-divinyl benzene copolymer acidic ion exchange resin. Suitably, the admixture in the line 34 will contain about 2 to about 15 parts of recycle isobutylene per 100 parts of first distillation fraction 32.

Etherification reaction conditions established in the isobutylene conversion zone 40 include, for example, a temperature of about 35° to about 130° C., and more preferably from about 40° to about 90° C., a pressure of about 50 to about 500 psia, and more preferably from about 150 to about 250 psia, and a contact time of about 0.5 to about 4 volumes of first distillation fraction per volume of solid resin etherification catalyst per hour. As a consequence, a portion of the methanol and isobutylene contained in the first distillation fraction 32 will be converted to methyl tertiary butyl ether. Typically, the conversion will amount to about 20 to about 85 wt. %, based on the isobutylene.

As a consequence, there will be formed an isobutylene conversion product discharged in the isobutylene conversion zone 40 by a line 42 leading to a methanol solvent extraction zone 50.

The composition of a representative feedstock and a representative isobutylene conversion product may be characterized as follows:

| ISOBUTYLENE FEEDSTOCK AND CONVERSION PRODUCT | | |
|---|---|---|
| Component | Feed, wt. % | Product, wt. % |
| Water | 0.5 wt. % | 0.4 wt. % |
| Methanol | 13.5 wt. % | 8.0 wt. % |
| Isobutylene | 12.0 wt. % | 2.5 wt. % |
| TBA | 0.9 wt. % | 1.0 wt. % |
| MTBE | 70.4 wt. % | 85.5 wt. % |
| Other | 2.7 wt. % | 2.6 wt. % |

In accordance with the present invention, the isobutylene conversion product 42 together with recycle isobutylene charged by a recycle line 83 is charged to a manifold 44 and thence via line 46 to a methanol solvent extraction zone 50 where it is countercurrently contacted with water introduced into the solvent extraction zone 50 by a charge line 52 controlled by a valve 54.

Within the methanol solvent extraction zone 50, solvent extraction conditions are established for countercurrent solvent extraction including a ratio of isobutylene to water within the range of about 0.8 to about 1.8 volumes of isobutylene per volume of water per hour, and more preferably a ratio of about 1.0 to about 1.5 volumes of isobutylene per volume of water. Extractive conditions to be established may suitably include a temperature of about 20° to about 60° C., and more preferably from about 30° to about 40° C., and a pressure of about 50 to about 500 psia, and more preferably from about 50 to about 150 psia.

As a consequence, a supernatant raffinate will be formed which is withdrawn from the methanol solvent extraction zone 50 by line 60. The extract is discharged from the solvent extraction zone 50 by way of a bottoms charge line 64 leading to a third methyl tertiary butyl ether distillation zone 70.

Within the second methyl tertiary butyl ether purification distillation zone 62, distillation conditions are established including a liquid ref lux temperature of about 30° to about 60° C., and more preferably from about 40° to about 55° C., a reboiler temperature of about 100° to about 140° C., and more preferably from about 125° to about 135° C. and a pressure of about 70 to about 120 psia, and more preferably from about 90 to about 110 psia, to thereby form a lighter distillation fraction 66 discharged from the second distillation zone 62 and a heavier fourth distillation fraction 68 consisting essentially of product, namely methyl tertiary butyl ether.

The third distillation fraction 66 will comprise a mixture of isobutylene and water and is suitably charged to a decantation zone 80 where it can settle to form a supernatant isobutylene phase withdrawn from the decantation zone 80 by way of a line 82. Water is discharged in the decantation zone 80 by way of a water discharge line 84 and is suitably purged from the system. A portion of the isobutylene in the line 82 is recycled by way of manifold 86, line 89 controlled by valve 87, manifold 33 and line 35 to the isobutylene conversion reaction zone 40 as a first isobutylene recycle fraction and another portion of the isobutylene in the line 82 is recycled to the methanol solvent extraction zone 50 through a branch line 83 controlled by a valve 85 as a second isobutylene recycle fraction. Suitably, about 10 to about 15 wt. % of the isobutylene in line 82 is discharged from manifold 86 as the first isobutylene recycle fraction and about 90 to about 85 wt. % is discharged as the second isobutylene recycle fraction.

The extract 64 charged to the third distillation zone 70 will comprise methyl tertiary butyl ether, methanol and water, and is suitably fractionated therein under distillation conditions including a liquid reflux temperature of about 30° to about 90° C., and more preferably from about 50° to about 75° C., and a reboiler temperature of about 80° to about 120° C., and more preferably from about 105° to about 115° C., and a pressure of about 15 to about 60 psia, and more preferably from about 40 to about 50 psia, to form a fifth lighter distillation fraction 72 comprising methyl tertiary butyl ether which may suitably be charged to the manifold 44 for the charge line 46 to the methanol solvent extraction zone 50. A sixth heavier distillation fraction comprising water and methanol is discharged from the third distillation zone 70 by a line 74 leading to a fourth distillation zone 90. The sixth distillation fraction charged to the fourth methanol distillation zone 90 is fractionated therein under distillation conditions which may suitably include a liquid ref lux temperature of about 30° to about 80° C., and more preferably from about 60° to about 75° C., a reboiler temperature of about 100° to about 140° C., and more preferably from about 110° to about 120° C., and a pressure of about 15 to about 60 psia, and more preferably from about 20 to about 30 psia, into a seventh lighter distillation fraction 92 which may be suitably charged to a manifold 93 and from thence by line 112 to the manifold 12 for recycle to the etherification reaction zone 10 through feed line 14. A heavier distillation fraction consisting essentially of water is discharged from the fourth methanol distillation zone by way of a line 94 and may be discharged from the system through manifold 95 and water discharge line 96.

The second distillation fraction 34 discharged from the first MTBE distillation zone 30 in accordance with the present invention is charged to a fifth tertiary butyl alcohol recovery distillation zone 100 where it is fractionated under distillation conditions including a liquid reflux temperature of about 35° to about 170° C., and more preferably about 140° to about 150° C., and a reboiler temperature of about 100° to about 190° C., more preferably about 170° to about 180° C., and at a pressure of about 15 to about 190 psia, and more preferably about 110 to about 160 psia, into a ninth distillation fraction discharged in the fifth distillation zone 100 by a line 102 leading to manifold 103 and a tenth heavier distillation fraction comprising a third water fraction discharged from the distillation zone 100 by a line 106 leading by way of manifold 95 to the water discharge line 96.

In accordance with one embodiment of the present invention, the ninth distillation fraction 102 is charged to a manifold 103 provided with a discharge line 118 controlled by a valve 116 leading to the feed manifold 12 so that the methanol can be directly charged to the etherification reaction zone 10 from manifold 12 through feed line 14. A second branch line 120 controlled by a valve 98 is provided which leads from manifold 103 to the feed manifold 44 for the methanol extraction zone 50 so that all or a portion of the ninth distillation fraction 102 may be recycled to the manifold 44.

EXAMPLE

The invention will be further illustrated by the following specific example(s), which are given by way of illustration and not as a limitation on the scope of this invention. Where parts are mentioned, they are parts by weight.

In accordance with a preferred embodiment of the present invention, a tertiary butyl alcohol feedstock is continuously charged to peroxide decomposition zone 11 by a line 13 where it is thermally treated under thermal di-tertiary butyl peroxide decomposition conditions including a temperature of about 100° to about 200° C., a pressure of about 80 to about 500 psia and a flow rate of about 0.5 to 4 volumes of feedstock per reactor volume per hour to thereby provide a substantially peroxides-free tertiary butyl alcohol reaction product.

The peroxides-contaminated feedstock and the substantially peroxides-free reaction product discharged from the peroxide decomposition zone 11 will typically have compositions as follows:

PEROXIDE DECOMPOSITION ZONE FEED AND PRODUCT

| Component | Feed (wt. %) | Product (wt. %) |
| --- | --- | --- |
| DTBP[1] | 0.87 | 0.02 |
| TBA[2] | 97.2 | 97.2 |
| Water | 0.1 | 0.01 |
| Other[3] | 1.8 | 2.6 |

[1]Ditertiary butyl peroxide
[2]Tertiary butyl alcohol
[3]Includes acetone, tertiary butyl formate, isopropyl alcohol, etc.

The substantially peroxides-free tertiary butyl reaction product 17 is charged to the manifold 12 together with fresh methanol feedstock 15 and the recycle fraction 112 in amounts, for example, such that the charge ratio of methanol to tertiary butyl alcohol in the feed line 14 amounts to about 2 moles of methanol per mole of tertiary butyl alcohol.

The feed mixture is discharged from the manifold 12 by a line 14 leading to etherification reaction zone reactor 10 containing a bed of a suitable etherification catalyst, such as Amberlyst 15 catalyst. Within the etherification reaction zone, the feedstock is passed through the etherification reaction bed on a continuous basis under reaction conditions, as described above, to thereby provide a reaction product having the following composition:

ETHERIFICATION REACTION ZONE REACTION PRODUCT

| Component | wt. % (approx.) |
| --- | --- |
| Methanol | 27.6 |
| TBA | 14.1 |
| Water | 14.0 |
| Isobutylene | 3.5 |
| MTBE | 34.5 |
| Acetone | 0.4 |
| 2-Propanol | 5.7 |

The etherification zone reaction product is discharged from the reaction zone 10 by a line 20 leading to first methyl tertiary butyl ether distillation zone 30 where the fraction 20 is separated into a substantially anhydrous first lighter distillation fraction 32 comprising about 0.1 wt. % of water, about 12.4 wt. % isobutylene, about 13.1 wt. % methanol and about 73.4 wt. % MTBE, and a second heavier fraction comprising about 37 wt. % methanol, about 26.0 wt. % tertiary butyl alcohol, about 26 wt. % water, 11 wt. % isopropanol and about 0.5 wt. % of other components.

The first distillation fraction 32 along with recycle isobutylene 83 is continuously charged to an isobutylene conversion zone 40 through the line 34 and brought into contact therein with a solid resin etherification catalyst, such as Amberlyst 15 catalyst, under conversion conditions, as described above, including a temperature of about 160° F. and a LHSV of about 5 to thereby convert about 75 wt. % of the isobutylene and a portion of the methanol in the first distillation fraction to MTBE and to form an isobutylene conversion product which is discharged from the isobutylene reaction zone 40 by a line 42 and which typically has the following composition:

| ISOBUTYLENE CONVERSION FEED AND PRODUCT, wt. % | | |
|---|---|---|
| Component | Feed | Product |
| Water | 0.1 | 0.15 |
| Isobutylene | 12.0 | 3.0 |
| MTBE | 73.0 | 86.0 |
| Methanol | 13.5 | 8.0 |
| TBA | 0.4 | 0.51 |

The isobutylene conversion fraction 42 and the isobutylene recycle-fraction 83 are continuously charged to the manifold 44 by a line 46 leading from manifold 45. The isobutylene mixture is discharged from the manifold 44 together with recycle fraction 120 and recycle fraction 72 by a feed line 46 leading to methanol extraction zone 50 in the ratio of about 2 parts of isobutylene conversion product per part of recycle isobutylene. Water is charged to the methanol extraction zone 50 by a water charge line 52 in an amount such that the ratio of water to isobutylene and isobutylene conversion product in the methanol extraction zone 50 is in the range of about 0.1 to about 0.3 parts of water per part of isobutylene.

Within the methanol extraction zone, the methanol is extracted from the isobutylene conversion product under extraction conditions as described above to thereby provide an overhead (raffinate) fraction 60 comprising isobutylene and methyl tertiary butyl ether and a extract 64 comprising methanol and water.

The raffinate is fed by a line 60 to a second methyl tertiary butyl ether purification distillation zone 62 where it is resolved by distillation into a third lighter distillation fraction 66 comprising isobutylene and water and into a fourth heavier distillation fraction 68 consisting essentially of methyl tertiary butyl ether which is discharged as product.

The third distillation fraction 66 is charged to a decantation separation zone 80 where it is permitted to settle and is resolved into an isobutylene fraction 82 and a first water fraction 84 which is discharged from the system.

The isobutylene fraction 82 is suitably recycled to the isobutylene conversion zone 40 in admixture with the first distillation fraction 32 and to the feed to the methanol extraction zone.

Typically, about 2 to about 5 parts of recycle isobutylene from the line 89 will be mixed with 100 parts of overhead product from the first distillation fraction 32.

The extract 64 is continuously charged to a third methyl tertiary butyl ether distillation zone 70 where it is separated into a lighter fifth distillation fraction 72 comprising methyl tertiary butyl ether and a sixth heavier distillation fraction 74 comprising methanol and water. The fraction 74 is continuously charged to a fourth methanol distillation zone 90 wherein it is separated by fractional distillation into a seventh lighter distillation fraction 92 comprising methanol and an eighth distillation fraction comprising water which is discharged by a line 94. In accordance with the preferred embodiment of the present invention, the fraction 92 together with fraction 118 is charged by a line 112 to feed manifold 12.

The second distillation fraction 34 from the first MTBE distillation zone 30 is continuously charged to a fifth tertiary butyl alcohol recovery distillation zone 100 where it is separated into a ninth lighter distillation fraction 102 comprising methanol, tertiary butyl alcohol and water and a tenth heavier distillation fraction 106 comprising water. The tenth heavier distillation fraction is discharged by a line 106 and the water in line 106, together with the water in line 94, may suitably discharge from the system from manifold 95 through water discharge line 96.

ADDITIONAL EXAMPLES

A series of experiments were conducted using a stainless steel tubular reactor (0.51"×29") which was electrically heated. Liquid feed was pumped into the bottom of the reactor. Pressure was regulated with a Go Back Pressure Regulator. The liquid feed was pumped with a Milton Roy mini Pump®.

The feedstocks that were used, the experimental reaction conditions and the results that were obtained are set forth in the following tables.

TABLE I

RUN 6617-64
GC Analysis of Reactor Effluent from
MTBE Finishing Reactor Test, 200 psi, Amberlyst 15
Simulated Feed (1% H$_2$O, 73% MTBE, 9.2% Isobutylene, 14.5% MeOH + Others)

| Hours | Sample # | Temp. ° F. | LHSV | Water (wt. %) | MeOH (wt. %) | Iso-C4 (wt. %) | TBA (wt. %) | MTBE (wt. %) | Iso-C4 Conv. (%) | HTBE Select. (%) |
|---|---|---|---|---|---|---|---|---|---|---|
| 20 | 1 | 120 | 2 | 0.51 | 11.50 | 1.85 | 2.94 | 81.64 | 80.02 | 76.92 |
| 24 | 2 | " | 2 | 0.50 | 11.48 | 1.85 | 2.94 | 81.65 | 80.05 | 76.93 |
| 44 | 3 | " | 5 | 0.57 | 12.80 | 4.35 | 2.74 | 77.92 | 52.94 | 67.85 |
| 48 | 4 | " | 5 | 0.27 | 11.36 | 4.60 | 2.98 | 80.28 | 50.24 | 73.43 |
| 69 | 5 | " | 10 | 0.46 | 12.26 | 7.35 | 1.93 | 76.51 | 20.57 | 71.71 |
| 73 | 6 | " | 10 | 0.45 | 11.96 | 6.95 | 1.86 | 76.91 | 24.84 | 74.98 |

TABLE I-continued

RUN 6617-64
GC Analysis of Reactor Effluent from
MTBE Finishing Reactor Test, 200 psi, Amberlyst 15
Simulated Feed (1% H$_2$O, 73% MTBE, 9.2% Isobutylene, 14.5% MeOH + Others)

| | | | | | | | | | | |
|---|---|---|---|---|---|---|---|---|---|---|
| 94 | 7 | 180 | 2 | 0.27 | 11.31 | 3.65 | 2.73 | 81.12 | 60.55 | 77.62 |
| 98 | 8 | " | 2 | 0.62 | 12.60 | 3.65 | 2.62 | 79.03 | 60.54 | 73.24 |
| 116 | 9 | " | 5 | 0.70 | 12.95 | 3.70 | 2.70 | 79.18 | 60.01 | 72.88 |
| 120 | 10 | " | 5 | 0.23 | 11.55 | 3.51 | 2.62 | 80.43 | 62.03 | 77.07 |
| 140 | 11 | " | 10 | 0.22 | 11.43 | 3.65 | 2.60 | 80.49 | 59.03 | 72.17 |
| 144 | 12 | " | 10 | 0.41 | 11.30 | 3.72 | 2.54 | 80.42 | 58.24 | 72.68 |
| 164 | 13 | 160 | 2 | 0.58 | 11.86 | 2.53 | 2.56 | 80.77 | 71.60 | 73.57 |
| 168 | 14 | " | 2 | 0.57 | 11.87 | 2.57 | 2.51 | 80.79 | 71.17 | 74.21 |
| 188 | 15 | " | 5 | 0.62 | 12.01 | 2.71 | 2.58 | 80.36 | 69.60 | 71.94 |
| 192 | 16 | " | 10 | 0.54 | 12.24 | 3.27 | 2.53 | 79.68 | 63.30 | 69.78 |

| Feed Sample | Water (wt. %) | MeOH (wt. %) | Iso-C4 (wt. %) | TBA (wt. %) | MTBE (wt. %) |
|---|---|---|---|---|---|
| FS-1 | 1.02 | 14.49 | 9.25 | 0.74 | 72.91 |
| FS-2 | 0.64 | 13.19 | 8.90 | 0.77 | 74.83 |

TABLE II

RUN 6617-69
GC Analysis of Reactor Effluent from
MTBE Finishing Reactor Test, 200 psi, Amberlyst 15
Simulated Feed (0.3% H$_2$O, 75% MTBE, 8.6% Isobutylene, 14.7% MeOH + Others)

| Sample # | Temp. °F. | LHSV | Water (wt. %) | MeOH (wt. %) | Iso-C4 (wt. %) | TBA (wt. %) | MTBE (wt. %) | Iso-C4 Conv. (%) | MTBE Select. (%) |
|---|---|---|---|---|---|---|---|---|---|
| 1 | 122 | 2 | — | 10.29 | 1.70 | 1.26 | 85.11 | 81.19 | 94.76 |
| 2 | " | 2 | 0.23 | 11.27 | 1.62 | 1.25 | 83.84 | 82.05 | 94.27 |
| 3 | " | 5 | 0.26 | 12.54 | 3.63 | 1.79 | 80.04 | 59.78 | 81.43 |
| 4 | " | 5 | 0.21 | 12.57 | 3.75 | 1.29 | 81.55 | 58.41 | 91.84 |
| 5 | " | 10 | 0.24 | 13.86 | 6.18 | 1.22 | 77.81 | 31.55 | 85.38 |
| 6 | " | 10 | 0.10 | 12.86 | 5.90 | 2.30 | 77.22 | 34.64 | 57.27 |
| 7 | 180 | 2 | 0.41 | 12.58 | 3.43 | 1.30 | 81.18 | 61.96 | 91.27 |
| 8 | " | 2 | — | 11.33 | 3.30 | 1.27 | 83.19 | 63.41 | 93.59 |
| 9 | " | 5 | 0.25 | 11.41 | 3.32 | 1.45 | 81.91 | 63.25 | 90.01 |
| 10 | " | 5 | 0.42 | 12.71 | 3.48 | 1.53 | 80.82 | 61.47 | 87.09 |
| 11 | " | 10 | — | 11.37 | 3.46 | 1.19 | 82.07 | 61.65 | 93.78 |
| 12 | " | 10 | 0.31 | 12.70 | 3.59 | 1.24 | 81.17 | 60.25 | 92.11 |

| Feed Sample | Water (wt. %) | MeOH (wt. %) | Iso-C4 (wt. %) | TBA (wt. %) | MTBE (wt. %) |
|---|---|---|---|---|---|
| FS-1 | — | 13.73 | 9.02 | 0.78 | 74.79 |

TABLE III

RUN 6819-1
GC Analysis of Reactor Effluent from
MTBE Finishing Reactor Test, 200 psi, Amberlyst 15
Simulated Feed (0.1% H$_2$O, 75% MTBE, 8.6% Isobutylene, 14.9% MeOH + Others)

| Sample # | Temp. °F. | LHSV | Water (wt. %) | MeOH (wt. %) | Iso-C4 (wt. %) | TBA (wt. %) | MTBE (wt. %) | Iso-C4 Conv. (%) | MTBE Select. (%) |
|---|---|---|---|---|---|---|---|---|---|
| 1 | 118 | 2 | 0.39 | 11.53 | 1.83 | 1.01 | 83.49 | 80.58 | 97.79 |
| 2 | " | 2 | — | 9.96 | 1.79 | 1.11 | 85.31 | 81.02 | 97.08 |
| 3 | " | 5 | — | 10.95 | 4.04 | 0.96 | 82.21 | 57.19 | 98.27 |
| 4 | " | 5 | — | 11.03 | 3.94 | 0.96 | 82.27 | 58.23 | 98.16 |
| 5 | " | 10 | 0.16 | 14.14 | 6.40 | 1.57 | 76.98 | 32.09 | 72.43 |
| 6 | " | 10 | 0.21 | 13.84 | 6.41 | 0.91 | 75.89 | 32.00 | 93.71 |

| Feed Sample | Water (wt. %) | MeOH (wt. %) | Iso-C4 (wt. %) | TBA (wt. %) | MTBE (wt. %) |
|---|---|---|---|---|---|
| FS-1 | — | 13.25 | 9.43 | 0.84 | 74.70 |

TABLE IV

RUN 6819-4
GC Analysis of Reactor Effluent from
MTBE Finishing Reactor Test, 200 psi, Amberlyst 15
Simulated Feed (0.1% H₂O, 73.4% MTBE, 12.4% Isobutylene, 13.1% MeOH + Others)

| Sample # | Temp. °F. | LHSV | Water (wt. %) | MeOH (wt. %) | Iso-C4 (wt. %) | TBA (wt. %) | MTBE (wt.%) | Iso-C4 Conv. (%) | MTBE Select. (%) | DME in Sample ppm |
|---|---|---|---|---|---|---|---|---|---|---|
| 1 | 140 | 2 | 0.10 | 7.61 | 2.19 | 0.52 | 87.16 | 81.76 | 96.4 | 290 |
| 2 | " | 2 | 0.09 | 7.50 | 2.16 | 0.48 | 87.29 | 81.95 | 96.7 | 290 |
| 3 | " | 5 | — | 7.81 | 2.51 | 1.26 | 85.79 | 79.11 | 91.1 | |
| 4 | " | 5 | — | 7.78 | 2.48 | 0.93 | 86.15 | 79.32 | 93.4 | 300 |
| 5 | " | 10 | — | 8.74 | 4.16 | 0.67 | 83.74 | 65.34 | 94.4 | |
| 6 | " | 10 | 0.03 | 8.65 | 4.31 | 0.52 | 83.63 | 64.09 | 95.6 | 220 |
| 7 | 160 | 2 | — | 8.22 | 2.93 | 0.82 | 85.29 | 75.61 | 93.9 | 510 |
| 8 | " | 2 | 0.15 | 8.24 | 3.12 | 0.51 | 85.29 | 74.02 | 96.1 | 499 |
| 9 | " | 5 | — | 8.46 | 3.06 | 0.69 | 85.00 | 74.52 | 94.7 | 340 |
| 10 | " | 5 | — | 8.46 | 2.86 | 0.89 | 82.52 | 76.13 | 92.0 | 340 |
| 11 | " | 10 | — | 8.78 | 3.72 | 0.47 | 84.29 | 68.95 | 96.1 | 320 |
| 12 | " | 10 | 0.21 | 8.81 | 3.71 | 0.57 | 83.71 | 69.04 | 95.2 | 279 |
| 13 | 118 | 2 | 0.14 | 7.95 | 2.72 | 0.64 | 85.40 | 76.88 | 95.8 | 230 |
| 14 | " | 2 | — | 7.76 | 2.43 | 0.81 | 86.40 | 79.37 | 95.0 | 350 |
| 15 | " | 5 | 0.08 | 9.35 | 5.41 | 0.61 | 81.39 | 54.04 | 94.8 | 330 |
| 16 | " | 5 | — | 8.49 | 4.93 | 1.46 | 82.20 | 58.10 | 89.0 | 370 |
| 17 | " | 10 | — | 11.49 | 8.81 | 0.72 | 76.29 | 25.15 | 90.5 | 300 |
| 18 | " | 10 | — | 11.27 | 9.01 | 0.56 | 76.46 | 23.40 | 92.6 | 290 |
| 19 | 180 | 2 | 0.17 | 9.21 | 4.27 | 0.81 | 82.68 | 63.72 | 93.8 | 1630 |
| 20 | " | 2 | 0.27 | 9.31 | 4.24 | 0.63 | 83.26 | 63.98 | 94.1 | 1550 |
| 21 | " | 5 | 0.13 | 9.21 | 4.33 | 0.52 | 82.35 | 63.24 | 93.9 | 880 |
| 22 | " | 5 | — | 8.65 | 4.01 | 0.79 | 83.67 | 65.89 | 94.3 | 930 |
| 23 | " | 10 | — | 9.20 | 4.09 | 1.40 | 83.22 | 65.22 | 90.0 | 570 |
| 24 | " | 10 | — | 8.90 | 4.14 | 0.56 | 83.50 | 64.80 | 95.8 | 570 |

Summaries of Reactor Tests

Run 6617-64

Of interest, insofar as this run is concerned is the water content of the feed, which was 1%. The concentration of TBA in the reactor effluent varied from a low of 1.86 wt. % to a high of 2.94 wt. %.

Run 6617-69

In this run, the water content of the feed was 0.3%. The concentration of TBA in the reactor effluent varied from a low of 1.19 wt. % to a high of 2.30 wt. %.

Run 6819-1

In this run, the water content of the feed was 0.1%. The concentration of TBA in the reactor effluent varied from a low of 0.91 wt. % to a high of 1.57 wt. %.

Run 6819-4

In this run, the water content of the feed was 0.1%. The concentration of TBA in the reactor effluent varied from a low of 0.47 wt. % to a high of 1.46 wt. %.

The feed for Runs 6617-64, -69, and -69.1 contained <1.0 wt. % peroxides. The feed for run 6819-4 was free from peroxides. The presence of the peroxides did not significantly affect the results.

As the results of these tests demonstrate, a conversion product having a significantly reduced tertiary butyl alcohol content was obtained only in Run 6819-1 and Run 6819-4 where the feedstock contained only 0.1 wt. % of water. The presence of as little as 0.3 wt. % of water about doubled the tertiary butyl alcohol product when the results of Run 6617-69 are compared with the results of Run 6819-4.

These results are significant. Although tertiary butyl alcohol is a feedstock for the primary reaction, unreacted tertiary butyl alcohol can be substantially completely removed from methyl tertiary butyl ether when the reaction product is fractionated in the first methyl tertiary butyl ether distillation zone. The tertiary butyl alcohol thereafter becomes a harmful contaminant if it is reintroduced to the methyl tertiary butyl ether reaction product.

Through the provision of the process of the present invention, it is possible to convert the isobutylene formed as a by-product in the methyl tertiary butyl ether etherification reaction zone to additional methyl tertiary butyl ether in a finishing reactor with the formation of acceptably low levels of tertiary butyl alcohol contamination (e.g., 0.5 to 1 wt. %)

Having thus described our invention, what is claimed is:

1. A method for reducing the formation of tertiary butyl alcohol in a finishing reactor in the two-stage manufacture of methyl tertiary butyl ether from tertiary butyl alcohol and methanol, which comprises the steps of:

a) continuously passing a feed mixture comprising tertiary butyl alcohol and methanol through a methyl tertiary butyl ether etherification reaction zone containing a bed of a tertiary butyl alcohol/methanol etherification catalyst under etherification reaction conditions to form an etherification reaction product comprising unreacted methanol, unreacted tertiary butyl alcohol, water, isobutylene and methyl tertiary butyl ether, b) continuously charging said etherification reaction product to a first methyl tertiary butyl ether distillation zone and separating it therein under distillation conditions including a liquid reflux temperature of about 40° to about 80° C., a reflux ratio of about 1.0 to about 1.5, a reboiler temperature of about 95° to about 105° C., and a pressure of about 15 to about 60 psia, c) the distillation conditions being selected such that substantially all of the methyl tertiary butyl ether in the etherification reaction product is taken overhead and such that substantially all of the water exits at the bottom of the column, to thereby provide a substantially anhydrous first lighter distillation, substantially tertiary butyl alcohol-free fraction comprising about 5 to about 10 wt. % of isobutylene, about 10 to about 20 wt. % of methanol, about 0.05 to about 0.2 wt. % of water and about 70 to about 80 wt. % of methyl tertiary butyl ether and a second heavier distillation fraction comprising methanol, tertiary butyl alcohol and water, and d) continuously charging said first distillation fraction to a finishing reactor containing a solid resin isobutylene/methanol etherification catalyst and reacting the isobutylene and methanol to form an isobutylene conversion product comprising methyl tertiary butyl ether, unreacted methanol, unreacted isobutylene and not more than about 1 wt. % of tertiary butyl alcohol.

2. A method as in claim 1 wherein the methanol and tertiary butyl alcohol are charged to the methyl tertiary butyl ether etherification reaction zone in the molar ratio of about 1.1 to about 3.0 moles of methanol per mole of tertiary butyl alcohol.

3. A method as in claim 2 wherein the etherification catalysts in the methyl tertiary butyl ether etherification zone and in the finishing reactor are solid resin divinyl benzene cross-linked sulfonated polystyrene catalysts.

4. A method as in claim 3 wherein the methanol is reacted with the tertiary butyl alcohol in the methyl tertiary butyl ether etherification zone under conversion conditions including a temperature of about 80° C. to about 120° C. and a pressure of about 30 to 500 psia at a flow rate of about 0.5 to 20 volumes of feed mixture per volume of etherification catalyst per hour, and wherein the isobutylene reaction mixture is reacted in the finishing reactor under reaction conditions including a temperature of about 35° to about 130° C., a pressure of about 50 to 500 psia and a flow rate of about 0.5 to about 4 volumes of reaction mixture per volume of catalyst per hour.

5. A method for reducing the formation of tertiary butyl alcohol in a finishing reactor in the two-stage manufacture of methyl tertiary butyl ether from tertiary butyl alcohol and methanol, which comprises the steps of:

a) continuously passing a feed mixture comprising tertiary butyl alcohol and methanol through a methyl tertiary butyl ether etherification reaction zone containing a bed of a tertiary butyl alcohol/methanol etherification catalyst under etherification reaction conditions to form an etherification reaction product comprising unreacted methanol, unreacted tertiary butyl alcohol, water, isobutylene and methyl tertiary butyl ether, b) continuously charging said etherification reaction product to a first methyl tertiary butyl ether distillation zone and separating it therein under distillation conditions including a liquid reflux temperature of about 40° to about 80° C., a reflux ratio of about 1.0 to about 1.5, a reboiler temperature of about 95° to about 105° C., and a pressure of about 15 to about 60 psia, the distillation conditions being selected such that substantially all of the methyl tertiary butyl ether in the etherification reaction product is taken overhead and such that substantially all of the water exits at the bottom of the column, to thereby provide a substantially anhydrous first lighter distillation, substantially tertiary butyl alcohol-free fraction comprising isobutylene, methanol and methyl tertiary butyl ether, and a second heavier distillation fraction comprising methanol, tertiary butyl alcohol and water, (c) said first lighter distillation fraction comprising about 70 to 80 wt. % of methyl tertiary butyl ether, about 10 to 20 wt. % of methanol, about 5 to 10 wt. % of isobutylene and about 0.05 to about 0.2 wt. % of water, and d) continuously charging said first distillation fraction to a finishing reactor containing a solid resin isobutylene/methanol etherification catalyst and reacting the isobutylene and methanol to form an isobutylene conversion product comprising methyl tertiary butyl ether, unreacted methanol, unreacted isobutylene and not more than about 1 wt. % of tertiary butyl alcohol.

6. A method as in claim 5 wherein the etherification catalysts in the methyl tertiary butyl ether etherification zone and in the finishing reactor are solid resin divinyl benzene cross-linked sulfonated polystyrene catalysts.

7. A method as in claim 6 wherein the methanol is reacted with the tertiary butyl alcohol in the methyl tertiary butyl ether etherification zone under conversion conditions including a temperature of about 80° to about 120° C. and a pressure of about 30 to 500 psia at a flow rate of about 0.5 to 20 volumes of feed mixture per volume of etherification catalyst per hour, and wherein the isobutylene reaction mixture is reacted in the finishing reactor under reaction conditions including a temperature of about 35° to about 130° C., a pressure of about 50 to 500 psia and a flow rate of about 0.5 to about 4 volumes of reaction mixture per volume of catalyst per hour.

* * * * *